US010227573B2

(12) United States Patent
Scheller et al.

(10) Patent No.: US 10,227,573 B2
(45) Date of Patent: Mar. 12, 2019

(54) **DOMINANT NEGATIVE MUTATIONS OF *ARABIDOPSIS* RWA**

(71) Applicant: The Regents of the University of California, Oakland, CA (US)

(72) Inventors: Henrik Vibe Scheller, Millbrae, CA (US); Dominique Loque, Albany, CA (US); Soe Myat Htwe, Daly City, CA (US)

(73) Assignee: The Regents of the University of California, Oakland, CA (US)

( * ) Notice: Subject to any disclaimer, the term of this patent is extended or adjusted under 35 U.S.C. 154(b) by 406 days.

(21) Appl. No.: 14/213,761

(22) Filed: Mar. 14, 2014

(65) Prior Publication Data

US 2015/0051376 A1   Feb. 19, 2015

Related U.S. Application Data

(60) Provisional application No. 61/800,268, filed on Mar. 15, 2013.

(51) Int. Cl.
*C12N 15/82* (2006.01)
*C12N 9/10* (2006.01)

(52) U.S. Cl.
CPC ....... *C12N 9/1029* (2013.01); *C12N 15/8261* (2013.01); *Y02A 40/146* (2018.01)

(58) Field of Classification Search
None
See application file for complete search history.

(56) References Cited

U.S. PATENT DOCUMENTS

2008/0124445 A1*  5/2008  Davies ............... C07K 14/415
                                                     426/615
2012/0047601 A1*  2/2012  Scheller ............... A01H 5/10
                                                     800/278

FOREIGN PATENT DOCUMENTS

WO    2012103555 A3    8/2012

OTHER PUBLICATIONS

Manabe et al (Loss-of-Function Mutation of Reduced Wall Acetylation2 in *Arabidopsis* Leads to Reduced Cell Wall Acetylation and Increased Resistance to Botrytis cinerea. Plant Physiology, vol. 155, pp. 1068-1078, Mar. 2011).*
Robey et al (Effect of amino acid substitutions on the catalytic and regulatory properties of aspartate transcarbamoylase. Proc. Nati. Acad. Sci. USA. vol. 83, pp. 5934-5938, Aug. 1986).*
Otto et al (Substitution of amino acids Asp-85, Asp-212, and Arg-82 in bacteriorhodopsin affects the proton release phase of the pump and the pK of the Schiff base. Proc. Nadl. Acad. Sci. USA. vol. 87, pp. 1018-1022, Feb. 1990).*
Lee, et al., "The Four *Arabidopsis* Reduced Wall Acetylation Genes are Expressed in Secondary Wall-Containing Cells and Required for the Acetylation of Xylan." Plant Cell Physiol., 52 (8):1289-1301 (2011).
IUPAC-IUB "Commission of Biochemical Nomenclature." Biochem., 9:4022 (1970).
Aranantharaman and Aravind, "Novel eukaryotic enzymes modifying cell-surfacebiopolymers," Biol Direct, 5:1 (2010). DOI: 10.1186/1745-6150-5-1.

* cited by examiner

*Primary Examiner* — Medina A Ibrahim
*Assistant Examiner* — Wayne Zhong
(74) *Attorney, Agent, or Firm* — Robin C. Chiang; Lawrence Berkeley National Laboratory

(57) ABSTRACT

The present invention provides for dominant negative mutations of *Arabidopsis* REDUCING WALL ACETYLATION (RWA).

11 Claims, 2 Drawing Sheets

Specification includes a Sequence Listing.

DOMINANT NEGATIVE MUTATIONS OF *ARABIDOPSIS* RWA

CROSS-REFERENCE TO RELATED APPLICATIONS

This application claims priority to U.S. Provisional Patent Application Ser. No. 61/800,268, filed Mar. 15, 2013, which is hereby incorporated by reference in its entirety.

STATEMENT OF GOVERNMENTAL SUPPORT

The invention described and claimed herein was made utilizing funds supplied by the U.S. Department of Energy under Contract No. DE-AC02-05CH11231. The government has certain rights in this invention.

FIELD OF THE INVENTION

The present invention is in the field of plant gene expression.

BACKGROUND OF THE INVENTION

Xylan is one of the major polysaccharides in cellulosic biomass. There are four *Arabidopsis* REDUCED WALL ACETYLATION (RWA) genes which are shown to be involved in the acetylation of xylan during secondary wall biosynthesis. See Lee et al., "The Four *Arabidopsis* REDUCED WALL ACETYLATION Genes are Expressed in Secondary Wall-Containing Cells and Required for the Acetylation of Xylan", *Plant Cell Physiol* (2011) 52 (8): 1289-1301.

SUMMARY OF THE INVENTION

The present invention provides for a polypeptide comprising an amino acid sequence having a sequence identity equal to or more than 70% of one of the sequences of SEQ ID NO:1-4; wherein a conserved his residue of the polypeptide (indicated by the first circled His in FIG. 1, and which corresponds to position 191 of SEQ ID NO:3) is substituted with another amino acid and/or a conserved Arg residue of the polypeptide (indicated by the circled Arg in FIG. 1, and which corresponds to position 231 of SEQ ID NO:3) is substituted with another amino acid, and the polypeptide has the biological function of a dominant negative *Arabidopsis* RWA mutant. A dominant negative *Arabidopsis* RWA mutant essentially lacks RWA activity and affects other RWA proteins (which by themselves would be active) to be essentially inactive. In some embodiments, the dominant negative *Arabidopsis* RWA mutant has its RWA activity essentially lost but the folding and stability of the protein are not essentially affected.

The present invention also provides for a nucleic acid encoding the polypeptide of the present invention. In some embodiments, the nucleic acid is vector capable of stable maintenance in a host cell. The host cell can be a eukaryotic or a prokaryotic cell. The host cell can be an animal or plant cell. The host cell can be a mammalian, insect, or yeast cell. The host cell can be a eubacterial cell, such as *E. coli*. In some embodiments, the vector comprises nucleotide sequences which enable its stable maintenance in the host cell or integration into the genome of the host cell. The nucleic acid can further comprises transcriptional control sequences, such as a promoter, activation sequences, or the like, which enable the expression of the encoded polypeptide in the host cell. One skilled in the art is able to determine what sequences to use in a particular host cell. In some embodiments, the host cell is a plant cell, or a plant cell in a plant.

The present invention also provides for a method of constructing the polypeptide of the present invention.

The present invention also provides for a plant comprising a genetically modified plant cell expressing the polypeptide of the present invention, wherein the plant has a reduced acetylation of xylan compared to a plant that does not comprise the genetically modified plant cell. In some embodiments, the genetically modified plant cell is a fiber cell. In some embodiments, the plant provides for a greater yield of sugars when subjected to biomass pretreatment and/or saccharification compared to a plant that does not comprise the genetically modified plant cell.

The present invention also provides for a method of producing sugars comprising: (a) providing a plant of the present invention, (b) pretreating the plant to produce a pretreated biomass, (c) optionally recovering sugars from the pretreated biomass, and (c) optionally hydrolyzing the sugars to produce a fermentable sugar.

In some embodiments, the pretreating step comprises contacting the plant with an ionic liquid. In some embodiments, the recovering step comprises contacting pretreated biomass with one or more solvents. In some embodiments, the hydrolyzing step comprises contacting the plant with an enzyme capable of hydrolyzing the sugars into a fermentable sugar.

One aspect of the invention is that it allows one skilled in the art to use dominant traits to engineer plants with decrease cell wall acetylation in specific cell types. A key benefit of such an approach is that it can be applied with high precision in contrast to conventional approached such as silencing and mutant approaches.

The invention is useful to engineer plants for biofuel purposes and other uses of biomass as feedstocks for chemical industry. The invention is also useful for engineering of plants, such as sugar beet and potato, to yield more valuable byproducts of sugar/starch production. The invention could also be used to increase pathogen resistance. In some embodiments, the plants of the present invention have increased resistance to pathogens compared to a wild-type plant.

BRIEF DESCRIPTION OF THE DRAWINGS

The foregoing aspects and others will be readily appreciated by the skilled artisan from the following description of illustrative embodiments when read in conjunction with the accompanying drawings.

Figure 1:
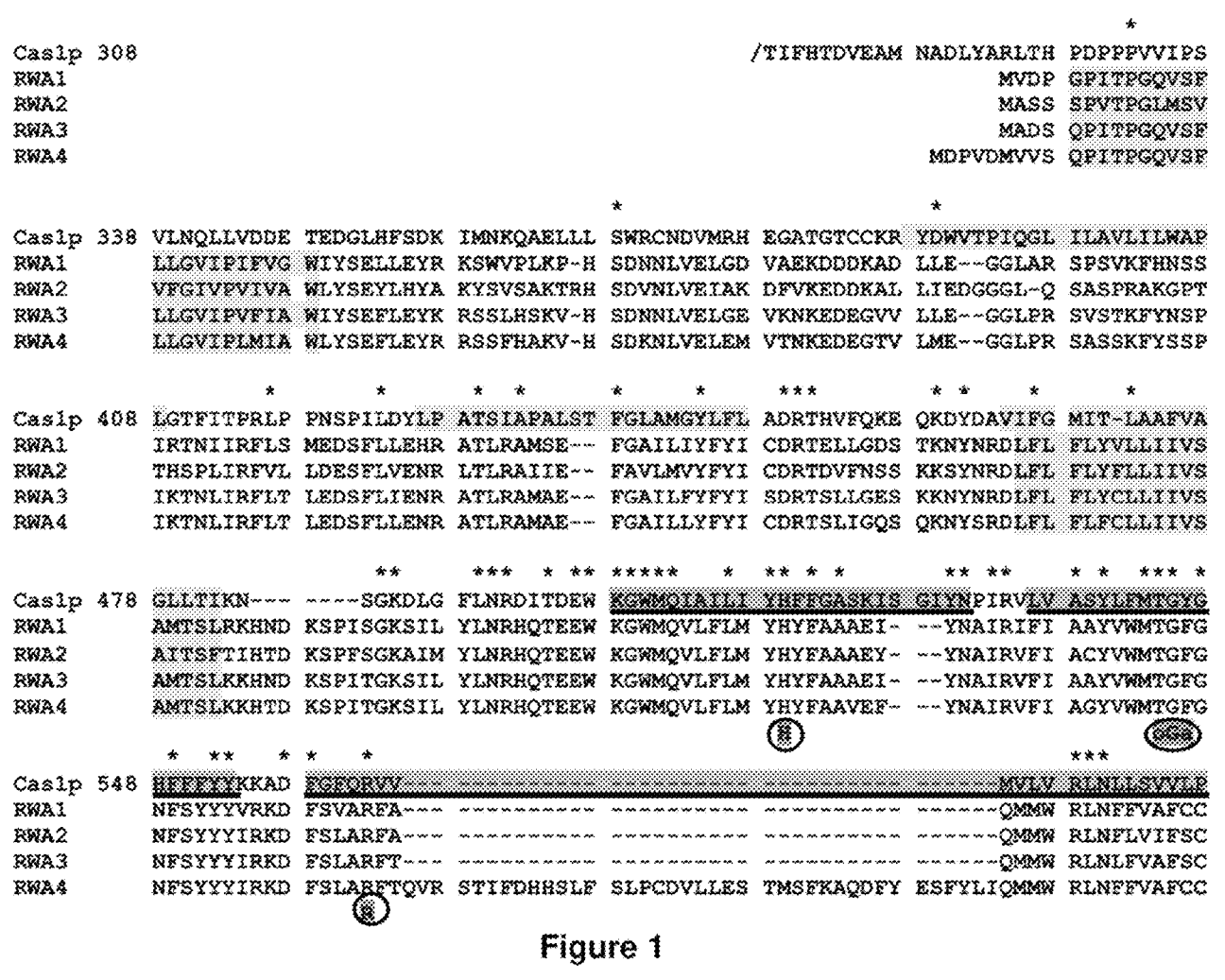
Figure 1:
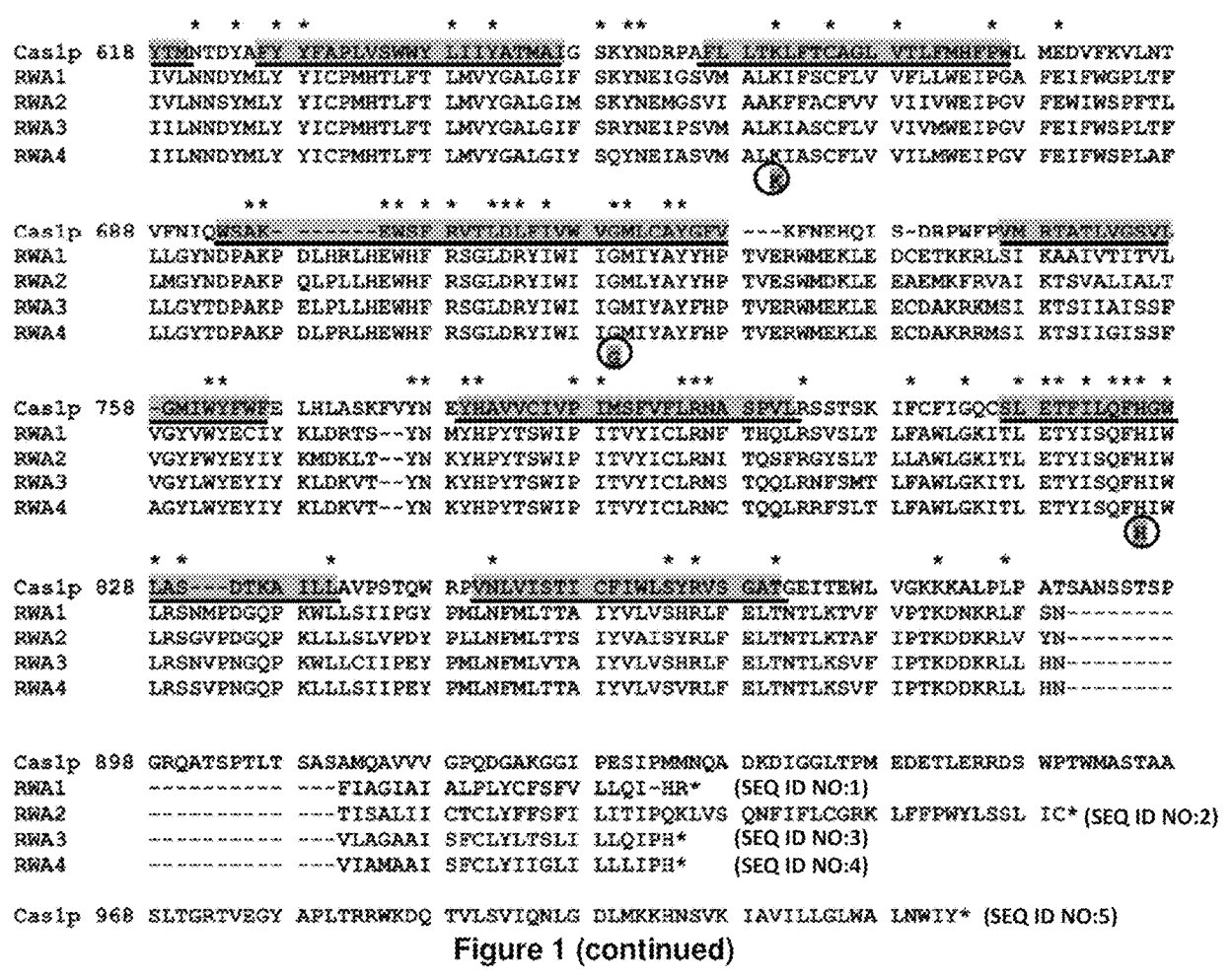

FIG. 1. Multiple sequence alignment of *Arabidopsis* RWA proteins and the C-terminal domain of *C. neoformans* Cas1p. All four RWA proteins have more than one gene model, but they differ only in minor details. The protein sequences used for the alignment correspond to the default gene models according to Signal-Salk T-DNA Express (http://signal.salk.edu/cgi-bin/tdnaexpress). Residues conserved in all five proteins are indicated with asterisks. The underlined resideus indicate transmembrane domains conserved in all 10TM acyltransferases, and the circled letters indicate residues conserved in all 10TM acyltransferases and proposed to constitute an inter-membrane active site (Anantharaman and Aravind, 2010). Yellow shading indicates additional transmembrane helices predicted in Cas1p and RWA proteins but not in all 10TM acyltransferases. The amino acid sequence of RWA1 is SEQ ID NO:1, RWA2 is SEQ ID NO:2, RWA3 is SEQ ID NO:3, RWA4 is SEQ ID NO:4, and Cas1p is SEQ ID NO:5.

DETAILED DESCRIPTION OF THE INVENTION

Before the invention is described in detail, it is to be understood that, unless otherwise indicated, this invention is not limited to particular sequences, expression vectors, synthetic TF, host microorganisms, or processes, as such may vary. It is also to be understood that the terminology used herein is for purposes of describing particular embodiments only, and is not intended to be limiting.

As used in the specification and the appended claims, the singular forms "a," "an," and "the" include plural referents unless the context clearly dictates otherwise. Thus, for example, reference to an "expression vector" includes a single expression vector as well as a plurality of expression vectors, either the same (e.g., the same operon) or different; reference to "cell" includes a single cell as well as a plurality of cells; and the like.

In this specification and in the claims that follow, reference will be made to a number of terms that shall be defined to have the following meanings:

The terms "optional" or "optionally" as used herein mean that the subsequently described feature or structure may or may not be present, or that the subsequently described event or circumstance may or may not occur, and that the description includes instances where a particular feature or structure is present and instances where the feature or structure is absent, or instances where the event or circumstance occurs and instances where it does not.

The terms "host cell" and "host microorganism" are used interchangeably herein to refer to a living biological cell that can be transformed via insertion of an expression vector. Thus, a host organism or cell as described herein may be a prokaryotic organism (e.g., an organism of the kingdom Eubacteria) or a eukaryotic cell. As will be appreciated by one of ordinary skill in the art, a prokaryotic cell lacks a membrane-bound nucleus, while a eukaryotic cell has a membrane-bound nucleus.

The term "heterologous" as used herein refers to a material, or nucleotide or amino acid sequence, that is found in or is linked to another material, or nucleotide or amino acid sequence, wherein the materials, or nucleotide or amino acid sequences, are foreign to each other (i.e., not found or linked together in nature).

The terms "expression vector" or "vector" refer to a compound and/or composition that transduces, transforms, or infects a host microorganism, thereby causing the cell to express nucleic acids and/or proteins other than those native to the cell, or in a manner not native to the cell. An "expression vector" contains a sequence of nucleic acids (ordinarily RNA or DNA) to be expressed by the host microorganism. Optionally, the expression vector also comprises materials to aid in achieving entry of the nucleic acid into the host microorganism, such as a virus, liposome, protein coating, or the like. The expression vectors contemplated for use in the present invention include those into which a nucleic acid sequence can be inserted, along with any preferred or required operational elements. Further, the expression vector must be one that can be transferred into a host microorganism and replicated therein. Particular expression vectors are plasmids, particularly those with restriction sites that have been well documented and that contain the operational elements preferred or required for transcription of the nucleic acid sequence. Such plasmids, as well as other expression vectors, are well known to those of ordinary skill in the art.

As used herein, the terms "nucleic acid sequence," "sequence of nucleic acids," and variations thereof shall be generic to polydeoxyribonucleotides (containing 2-deoxy-D-ribose), to polyribonucleotides (containing D-ribose), to any other type of polynucleotide that is an N-glycoside of a purine or pyrimidine base, and to other polymers containing nonnucleotidic backbones, provided that the polymers contain nucleobases in a configuration that allows for base pairing and base stacking, as found in DNA and RNA. Thus, these terms include known types of nucleic acid sequence modifications, for example, substitution of one or more of the naturally occurring nucleotides with an analog; internucleotide modifications, such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., arninoalklyphosphoramidates, aminoalkylphosphotriesters); those containing pendant moieties, such as, for example, proteins (including nucleases, toxins, antibodies, signal peptides, poly-L-lysine, etc.); those with intercalators (e.g., acridine, psoralen, etc.); and those containing chelators (e.g., metals, radioactive metals, boron, oxidative metals, etc.). As used herein, the symbols for nucleotides and polynucleotides are those recommended by the IUPAC-IUB Commission of Biochemical Nomenclature (*Biochem.* 9:4022, 1970).

The term "operably linked" refers to a functional linkage between a nucleic acid expression control sequence (such as a promoter) and a second nucleic acid sequence, wherein the expression control sequence directs transcription of the nucleic acid corresponding to the second sequence.

The present invention provides for a polypeptide comprising an amino acid sequence having a sequence identity equal to or more than 70% of the sequence of SEQ ID NO:1-4; wherein a conserved his residue of the polypeptide (indicated by the first circled His in FIG. 1, and which corresponds to position 191 of SEQ ID NO:3) is substituted with another amino acid and/or a conserved Arg residue of the polypeptide (indicated by the circled Arg in FIG. 1, and which corresponds to position 231 of SEQ ID NO:3) is substituted with another amino acid, and the polypeptide has the biological function of a dominant negative *Arabidopsis* RWA mutant. A dominant negative *Arabidopsis* RWA mutant essentially lacks RWA activity and affects other RWA proteins (which by themselves would be active) to be essentially inactive. In some embodiments, the dominant negative *Arabidopsis* RWA mutant has its RWA activity essentially lost but the folding and stability of the protein are not essentially affected.

In some embodiments, the conserved His (which corresponds to position 191 of SEQ ID NO:3) is substituted with an amino acid that does not have a hydrophilic side chain (such as Asp, Glu, Lys, Arg, Gly, Ser, Thr, Cys, Tyr, Asn and Gln). In some embodiments, the conserved His is substituted with a hydrophobic side chain (such as Leu, Ala, Val, Ile, Pro, Phe, Trp and Met). In some embodiments, the conserved His is substituted with Leu, Ala, Val, or Ile.

In some embodiments, the conserved Arg (which corresponds to position 231 of SEQ ID NO:3) is substituted with an amino acid that does not have a hydrophilic side chain (such as Asp, Glu, Lys, Arg, Gly, Ser, Thr, Cys, Tyr, Asn and Gln). In some embodiments, the conserved Arg is substituted with a hydrophobic side chain (such as Leu, Ala, Val, Ile, Pro, Phe, Trp and Met). In some embodiments, the conserved Arg is substituted with Leu, Ala, Val, or Ile.

In some embodiments, the polypeptide comprises an amino acid sequence having a sequence identity equal to or more than 70% of the sequence of SEQ ID NO:3; wherein the amino acid of the polypeptide at the analogous position 191 of SEQ ID NO:3 is not His and/or the amino acid of the polypeptide at the analogous position 231 of SEQ ID NO:3 is not Arg, and the polypeptide has the biological function of a dominant negative mutant of *Arabidopsis* RWA3.

In some embodiments, the amino acid of the polypeptide at the analogous position 191 of SEQ ID NO:3 is not an amino acid that has a hydrophilic side chain (such as Asp, Glu, Lys, Arg, Gly, Ser, Thr, Cys, Tyr, Asn and Gln). In some embodiments, the amino acid of the polypeptide at the analogous position 191 of SEQ ID NO:3 has a hydrophobic side chain (such as Leu, Ala, Val, Ile, Pro, Phe, Trp and Met). In some embodiments, the amino acid of the polypeptide at the analogous position 191 of SEQ ID NO:3 is Leu, Ala, Val, or Ile. In some embodiments, the amino acid of the polypeptide at the analogous position 191 of SEQ ID NO:3 is Ala.

In some embodiments, the amino acid of the polypeptide at the analogous position 231 of SEQ ID NO:3 is not an amino acid that has a hydrophilic side chain (such as Asp, Glu, Lys, His, Gly, Ser, Thr, Cys, Tyr, Asn and Gln). In some embodiments, the amino acid of the polypeptide at the analogous position 231 of SEQ ID NO:3 has a hydrophobic side chain (such as Leu, Ala, Val, Ile, Pro, Phe, Trp and Met). In some embodiments, the amino acid of the polypeptide at the analogous position 231 of SEQ ID NO:3 is Leu, Ala, Val, or Ile. In some embodiments, the amino acid of the polypeptide at the analogous position 231 of SEQ ID NO:3 is Ala.

In some embodiments, the amino acids of the polypeptide at the analogous positions 191 and 231 of SEQ ID NO:3 are both Ala.

The amino acid sequence of *Arabidopsis* RWA3 (gene model AT2G34410.1) is:

The present invention also provides for a nucleic acid encoding the polypeptide of the present invention. In some embodiments, the nucleic acid is vector capable of stable maintenance in a host cell. The host cell can be a eukaryotic or a prokaryotic cell. The host cell can be an animal or plant cell. The host cell can be a mammalian, insect, or yeast cell. The host cell can be a eubacterial cell, such as *E. coli*. In some embodiments, the vector comprises nucleotide sequences which enable its stable maintenance in the host cell or integration into the genome of the host cell. The nucleic acid can further comprises transcriptional control sequences, such as a promoter, activation sequences, or the like, which enable the expression of the encoded polypeptide in the host cell. One skilled in the art is able to determine what sequences to use in a particular host cell. In some embodiments, the host cell is a plant cell, or a plant cell in a plant.

Suitable plant promoters include, but are not limited to, the 35S promoter or a tissue-specific promoter, such as a fiber-specific promoter, such as the promoter of NST1. In a particular embodiment, a fiber-specific promoter, e.g. NST1, is operably linked to a polypeptide of the present invention to restrict the dominant negative protein to fiber cells and to avoid negative effects of downregulating acetylation in vessel or primary cell walls. In some embodiments, the NST1 promoter is combined with the NST1 artificial positive feedback loop in increase expression. In another embodiment, the polypeptide is operably linked to a strong secondary cell wall promoter in combination with a fiber specific promoter, which would control splicing of the target gene and thus its translation in fiber cells. The promoter can be heterologous to the gene encoding the polypeptide of the present invention.

One aspect of the invention is that it allows one skilled in the art to use dominant traits to engineer plants with decrease

```
                                                              (SEQ ID NO: 3)
  1    MADSQPITPG  QVSFLLGVIP  VFIAWIYSEF  LEYKRSSLHS  KVHSDNNLVE

51    LGEVKNKEDE  GVVLLEGGLP  RSVSTKFYNS  PIKTNLIRFL  TLEDSFLIEN

101    RATLRAMAEF  GAILFYFYIS  DRTSLLGESK  KNYNRDLFLF  LYCLLIIVSA

151    MTSLKKHNDK  SPITGKSILY  LNRHQTEEWK  GWMQVLFLMY  HYFAAAEIYN

201    AIRVFIAAYV  WMTGFGNFSY  YYIRKDFSLA  RFTQMMWRLN  LFVAFSCIIL

251    NNDYMLYYIC  PMHTLFTLMV  YGALGIFSRY  NEIPSVMALK  IASCFLVVIV

301    MWEIPGVFEI  FWSPLTFLLG  YTDPAKPELP  LLHEWHFRSG  LDRYIWIIGM

351    IYAYFHPTVE  RWMEKLEECD  AKRKMSIKTS  IIAISSFVGY  LWYEYIYKLD

401    KVTYNKYHPY  TSWIPITVYI  CLRNSTQQLR  NFSMTLFAWL  GKITLETYIS

451    QFHIWLRSNV  PNGQPKWLLC  IIPEYPMLNF  MLVTAIYVLV  SHRLFELTNT

501    LKSVFIPTKD  DKRLLHNVLA  GAAISFCLYL  TSLILLQIPH
```

The amino acid sequence of *Arabidopsis* RWA1 is depicted in FIG. 1 and is SEQ ID NO:1. The amino acid sequence of *Arabidopsis* RWA2 is depicted in FIG. 1 and is SEQ ID NO:2. The amino acid sequence of *Arabidopsis* RWA4 is depicted in FIG. 1 and is SEQ ID NO:4.

In some embodiments, the polypeptide comprises an amino acid sequence having a sequence identity equal to or more than 80%, 90%, 95%, or 99% of one of the sequences of SEQ ID NO:1-4.

cell wall acetylation in specific cell types. A key benefit of such an approach is that it can be applied with high precision in contrast to conventional approached such as silencing and mutant approaches.

In some embodiments, the plant is selected from the group consisting of *Arabidopsis*, poplar, eucalyptus, rice, corn, switchgrass, sorghum, millet, *miscanthus*, sugarcane, pine, alfalfa, wheat, soy, barley, turfgrass, tobacco, hemp, bamboo, rape, sunflower, willow, and *Brachypodium*.

In some embodiments, the present invention provides plants, plant cells, seeds, flowers, leave, fruit, or biomass comprising plant tissue engineered to have reduced acetylation of xylan.

In another aspect, the present invention provides methods of obtaining an increased amount of soluble sugars from a plant in a saccharification reaction. In some embodiments, the method comprises subjecting a plant engineered to have reduced acetylation of xylan to a saccharification reaction, thereby increasing the amount of soluble sugars that can be obtained from the plant as compared to a wild-type plant.

In another aspect, present invention provides methods of engineering a plant having reduced acetylation of xylan that is substantially localized to the vessels of xylem tissue of the plant.

Suitable host cells, promoters, nucleotide control sequences, and the like, and techniques thereof, are taught in PCT International Patent Application No. PCT/US2012/023182, which is hereby incorporated by reference.

In some embodiments, the polypeptide comprises altering the residue Arg-231 in *Arabidopsis* RWA3 to Ala, which destroys the activity of the protein without affecting its folding nor its stability. The gene encoding the altered polypeptide is then introduced into *Arabidopsis*, which results in a downregulation of acetylation. It is believed the mutated RWA3 protein competes with endogenous RWA proteins (not only RWA3) in acetyltransferase complexes. Similar sites in other RWA genes or RWA genes could have been used with the same result. The site to mutagenize is predicted from alignment of acetyltransferase related proteins from a range of species (described in a paper by Anantharaman and Aravid, Biol Direct 5 (2010), 1; which is hereby incorporated by reference) to be important for activity.

The mutagenized proteins are tested in *Arabidopsis* wild-type and rwa1/rwa3/rwa4 triple mutant to determine their ability to complement and their possible dominant negative function. The successful use for downregulation of acetylation shows that the dominant negative method is a feasible method for altering plant cell wall structure. It is predicted that the same general approach can be used for other polymers, especially to downregulate xylan biosynthesis in biomass for saccharification or to reduce cellulose crystallinity and recalcitrance.

The invention is useful to engineer plants for biofuel purposes and other uses of biomass as feedstocks for chemical industry. The invention is also useful for engineering of plants, such as sugar beet and potato, to yield more valuable byproducts of sugar/starch production. The invention could also be used to increase pathogen resistance.

It is to be understood that, while the invention has been described in conjunction with the preferred specific embodiments thereof, the foregoing description is intended to illustrate and not limit the scope of the invention. Other aspects, advantages, and modifications within the scope of the invention will be apparent to those skilled in the art to which the invention pertains.

All patents, patent applications, and publications mentioned herein are hereby incorporated by reference in their entireties.

The invention having been described, the following examples are offered to illustrate the subject invention by way of illustration, not by way of limitation.

Example 1

Overexpression of RWA3 with a mutation changing Arg-231 to Ala resulted in a protein that is not only unable to complement the rwa1/rwa3/rwa4 triple mutant but result in smaller growth in both wild-type and triple mutant genetic background.

The following mutations listed in Table 1 were made:

TABLE 1

| Position in At2g34410.1 | Original amino acid | Changed amino acid | Effect |
|---|---|---|---|
| 191 | His | Ala | Dominant negative effect |
| 213-215 | Thr-Gly-Phe | Ala-Ala-Leu | Mutated protein is not active, but no dominant negative effect observed |
| 231 | Arg | Ala | Dominant negative effect |
| 349 | Gly | Ala | The mutated protein is functional and no dominant negative effect observed |

Analyses are made to determine complementation and dominant negative effects. They include the transformation of wild type and rwa1/rwa3/rwa4 triple mutant with mutated RWA3 under control of 35S promoter, the measurement of growth (rosette size) and acetate level in leaves, and the measurement of acetate in stems.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

We claim:

1. A polypeptide comprising an amino acid sequence having
   (a) a sequence identity equal to or more than 70% of SEQ ID NO: 3;
   (b) P9, S44, L65, L90, L97, T103, A106, F110, Y116, D121, R122, T123, K131, Y133, F138, L145, G165, K166, L171, N172, R173, T176, E178, W179, K180, G181, W182, M183, Q184, L188, Y190, F193, A195, Y199, N200, I202, R203, A207, Y209, M212, T213, G214, G216, F218, Y221, Y222, D226, F237, R238, L239, N240, N251, Y254, Y257, Y258, L268, Y271, S278, Y280, N281, K290, C294, V298, P305, E309, A325, K326, E334, W335, F337, R338, L341, D342, R343, I345, G349, M350, A353, Y354, W392, Y393, Y407, H408, P415, I416, L422, R423, N424, R430, F437, G441, L445, E446, T447, I449, Q451, F452, H453, W455, L456, S458, L468, N479, S491, R493, I498, K509, and L514 of SEQ ID NO:3; and
   (c) the His at position 191 and/or the Arg at position 231 of SEQ ID NO: 3 substituted with a Leu, Ala, Val, or Ile,
   wherein the polypeptide has the biological function of a dominant negative *Arabidopsis* REDUCING WALL ACETYLATION (RWA) mutant.

2. The polypeptide of claim 1, wherein the residue at the position of the polypeptide corresponding to position 191 is Leu, Ala, Val, or Ile.

3. The polypeptide of claim 2, wherein the residue at the position of the polypeptide corresponding to position 191 is Ala.

4. The polypeptide of claim 1, wherein the residue at the position of the polypeptide corresponding to position 231 is Leu, Ala, Val, or Ile.

5. The polypeptide of claim 4, wherein the residue at the position of the polypeptide corresponding to position 231 is Ala.

6. The polypeptide of claim 1, wherein the residue at the position of the polypeptide corresponding to position 191 is Ala, and the residue at the position of the polypeptide corresponding to position 231 is Ala.

7. The polypeptide of claim 1, wherein the polypeptide comprises an amino acid sequence having a sequence identity equal to or more than 80% of SEQ ID NO: 3.

8. The polypeptide of claim 1, wherein the polypeptide comprises an amino acid sequence having a sequence identity equal to or more than 90% of SEQ ID NO: 3.

9. The polypeptide of claim 1, wherein the polypeptide comprises an amino acid sequence having a sequence identity equal to or more than 95% of SEQ ID NO: 3.

10. The polypeptide of claim 1, wherein the polypeptide comprises an amino acid sequence having a sequence identity equal to or more than 99% of SEQ ID NO: 3.

11. The polypeptide of claim 1, wherein the polypeptide comprises an amino acid sequence identical to the sequence of SEQ ID NO: 3, except the His at position 191 and/or the Arg at position 231 is substituted with a Leu, Ala, Val, or Ile.

* * * * *

SEQUENCE LISTING

<160> NUMBER OF SEQ ID NOS: 5

<210> SEQ ID NO 1
<211> LENGTH: 540
<212> TYPE: PRT
<213> ORGANISM: Arabidopsis thaliana

<400> SEQUENCE: 1

Met Val Asp Pro Gly Pro Ile Thr Pro Gly Gln Val Ser Phe Leu Leu
1               5                   10                  15

Gly Val Ile Pro Ile Phe Val Gly Trp Ile Tyr Ser Glu Leu Leu Glu
            20                  25                  30

```
Tyr Arg Lys Ser Trp Val Pro Leu Lys Pro His Ser Asp Asn Asn Leu
         35              40              45

Val Glu Leu Gly Asp Val Ala Glu Lys Asp Asp Lys Ala Asp Leu
 50              55              60

Leu Glu Gly Gly Leu Ala Arg Ser Pro Ser Val Lys Phe His Asn Ser
 65              70              75              80

Ser Ile Arg Thr Asn Ile Ile Arg Phe Leu Ser Met Glu Asp Ser Phe
             85              90              95

Leu Leu Glu His Arg Ala Thr Leu Arg Ala Met Ser Glu Phe Gly Ala
            100             105             110

Ile Leu Ile Tyr Phe Tyr Ile Cys Asp Arg Thr Glu Leu Leu Gly Asp
         115             120             125

Ser Thr Lys Asn Tyr Asn Arg Asp Leu Phe Leu Phe Leu Tyr Val Leu
     130             135             140

Leu Ile Ile Val Ser Ala Met Thr Ser Leu Arg Lys His Asn Asp Lys
145             150             155             160

Ser Pro Ile Ser Gly Lys Ser Ile Leu Tyr Leu Asn Arg His Gln Thr
             165             170             175

Glu Glu Trp Lys Gly Trp Met Gln Val Leu Phe Leu Met Tyr His Tyr
         180             185             190

Phe Ala Ala Ala Glu Ile Tyr Asn Ala Ile Arg Ile Phe Ile Ala Ala
     195             200             205

Tyr Val Trp Met Thr Gly Phe Gly Asn Phe Ser Tyr Tyr Tyr Val Arg
     210             215             220

Lys Asp Phe Ser Val Ala Arg Phe Ala Gln Met Met Trp Arg Leu Asn
225             230             235             240

Phe Phe Val Ala Phe Cys Cys Ile Val Leu Asn Asn Asp Tyr Met Leu
             245             250             255

Tyr Tyr Ile Cys Pro Met His Thr Leu Phe Thr Leu Met Val Tyr Gly
         260             265             270

Ala Leu Gly Ile Phe Ser Lys Tyr Asn Glu Ile Gly Ser Val Met Ala
     275             280             285

Leu Lys Ile Phe Ser Cys Phe Leu Val Val Phe Leu Leu Trp Glu Ile
 290             295             300

Pro Gly Ala Phe Glu Ile Phe Trp Gly Pro Leu Thr Phe Leu Leu Gly
305             310             315             320

Tyr Asn Asp Pro Ala Lys Pro Asp Leu His Arg Leu His Glu Trp His
             325             330             335

Phe Arg Ser Gly Leu Asp Arg Tyr Ile Trp Ile Ile Gly Met Ile Tyr
         340             345             350

Ala Tyr Tyr His Pro Thr Val Glu Arg Trp Met Glu Lys Leu Glu Asp
     355             360             365

Cys Glu Thr Lys Lys Arg Leu Ser Ile Lys Ala Ala Ile Val Thr Ile
 370             375             380

Thr Val Leu Val Gly Tyr Val Trp Tyr Glu Cys Ile Tyr Lys Leu Asp
385             390             395             400

Arg Thr Ser Tyr Asn Met Tyr His Pro Tyr Thr Ser Trp Ile Pro Ile
             405             410             415

Thr Val Tyr Ile Cys Leu Arg Asn Phe Thr His Gln Leu Arg Ser Val
         420             425             430

Ser Leu Thr Leu Phe Ala Trp Leu Gly Lys Ile Thr Leu Glu Thr Tyr
     435             440             445
```

```
Ile Ser Gln Phe His Ile Trp Leu Arg Ser Asn Met Pro Asp Gly Gln
    450                 455                 460

Pro Lys Trp Leu Leu Ser Ile Ile Pro Gly Tyr Pro Met Leu Asn Phe
465                 470                 475                 480

Met Leu Thr Thr Ala Ile Tyr Val Leu Val Ser His Arg Leu Phe Glu
                485                 490                 495

Leu Thr Asn Thr Leu Lys Thr Val Phe Val Pro Thr Lys Asp Asn Lys
                500                 505                 510

Arg Leu Phe Ser Asn Phe Ile Ala Gly Ile Ala Ile Ala Leu Pro Leu
                515                 520                 525

Tyr Cys Phe Ser Phe Val Leu Leu Gln Ile His Arg
530                 535                 540

<210> SEQ ID NO 2
<211> LENGTH: 568
<212> TYPE: PRT
<213> ORGANISM: Arabidopsis thaliana

<400> SEQUENCE: 2

Met Ala Ser Ser Pro Val Thr Pro Gly Leu Met Ser Val Val Phe
1               5                   10                  15

Gly Ile Val Pro Val Ile Val Ala Trp Leu Tyr Ser Glu Tyr Leu His
                20                  25                  30

Tyr Ala Lys Tyr Ser Val Ser Ala Lys Thr Arg His Ser Asp Val Asn
                35                  40                  45

Leu Val Glu Ile Ala Lys Asp Phe Val Lys Glu Asp Lys Ala Leu
    50                  55                  60

Leu Ile Glu Asp Gly Gly Leu Gln Ser Ala Ser Pro Arg Ala Lys
65                  70                  75                  80

Gly Pro Thr Thr His Ser Pro Leu Ile Arg Phe Val Leu Leu Asp Glu
                85                  90                  95

Ser Phe Leu Val Glu Asn Arg Leu Thr Leu Arg Ala Ile Ile Glu Phe
                100                 105                 110

Ala Val Leu Met Val Tyr Phe Tyr Ile Cys Asp Arg Thr Asp Val Phe
                115                 120                 125

Asn Ser Ser Lys Lys Ser Tyr Asn Arg Asp Leu Phe Leu Phe Leu Tyr
                130                 135                 140

Phe Leu Leu Ile Ile Val Ser Ala Ile Thr Ser Phe Thr Ile His Thr
145                 150                 155                 160

Asp Lys Ser Pro Phe Ser Gly Lys Ala Ile Met Tyr Leu Asn Arg His
                165                 170                 175

Gln Thr Glu Glu Trp Lys Gly Trp Met Gln Val Leu Phe Leu Met Tyr
                180                 185                 190

His Tyr Phe Ala Ala Ala Glu Tyr Tyr Asn Ala Ile Arg Val Phe Ile
                195                 200                 205

Ala Cys Tyr Val Trp Met Thr Gly Phe Gly Asn Phe Ser Tyr Tyr Tyr
                210                 215                 220

Ile Arg Lys Asp Phe Ser Leu Ala Arg Phe Ala Gln Met Met Trp Arg
225                 230                 235                 240

Leu Asn Phe Leu Val Ile Phe Ser Cys Ile Val Leu Asn Asn Ser Tyr
                245                 250                 255

Met Leu Tyr Tyr Ile Cys Pro Met His Thr Leu Phe Thr Leu Met Val
                260                 265                 270

Tyr Gly Ala Leu Gly Ile Met Ser Lys Tyr Asn Glu Met Gly Ser Val
                275                 280                 285
```

```
Ile Ala Ala Lys Phe Phe Ala Cys Phe Val Val Ile Val Trp
    290                 295                 300
Glu Ile Pro Gly Val Phe Glu Trp Ile Trp Ser Pro Phe Thr Leu Leu
305                     310                 315                 320
Met Gly Tyr Asn Asp Pro Ala Lys Pro Gln Leu Pro Leu Leu His Glu
                325                 330                 335
Trp His Phe Arg Ser Gly Leu Asp Arg Tyr Ile Trp Ile Gly Met
            340                 345                 350
Leu Tyr Ala Tyr Tyr His Pro Thr Val Glu Ser Trp Met Asp Lys Leu
        355                 360                 365
Glu Glu Ala Glu Met Lys Phe Arg Val Ala Ile Lys Thr Ser Val Ala
370                 375                 380
Leu Ile Ala Leu Thr Val Gly Tyr Phe Trp Tyr Glu Tyr Ile Tyr Lys
385                 390                 395                 400
Met Asp Lys Leu Thr Tyr Asn Lys Tyr His Pro Tyr Thr Ser Trp Ile
                405                 410                 415
Pro Ile Thr Val Tyr Ile Cys Leu Arg Asn Ile Thr Gln Ser Phe Arg
                420                 425                 430
Gly Tyr Ser Leu Thr Leu Leu Ala Trp Leu Gly Lys Ile Thr Leu Glu
            435                 440                 445
Thr Tyr Ile Ser Gln Phe His Ile Trp Leu Arg Ser Gly Val Pro Asp
        450                 455                 460
Gly Gln Pro Lys Leu Leu Leu Ser Leu Val Pro Asp Tyr Pro Leu Leu
465                 470                 475                 480
Asn Phe Met Leu Thr Thr Ser Ile Tyr Val Ala Ile Ser Tyr Arg Leu
                485                 490                 495
Phe Glu Leu Thr Asn Thr Leu Lys Thr Ala Phe Ile Pro Thr Lys Asp
                500                 505                 510
Asp Lys Arg Leu Val Tyr Asn Thr Ile Ser Ala Leu Ile Ile Cys Thr
            515                 520                 525
Cys Leu Tyr Phe Phe Ser Phe Ile Leu Ile Thr Ile Pro Gln Lys Leu
        530                 535                 540
Val Ser Gln Asn Phe Ile Phe Leu Cys Gly Arg Lys Leu Phe Phe Pro
545                 550                 555                 560
Trp Tyr Leu Ser Ser Leu Ile Cys
                565

<210> SEQ ID NO 3
<211> LENGTH: 540
<212> TYPE: PRT
<213> ORGANISM: Arabidopsis thaliana

<400> SEQUENCE: 3

Met Ala Asp Ser Gln Pro Ile Thr Pro Gly Gln Val Ser Phe Leu Leu
1               5                   10                  15
Gly Val Ile Pro Val Phe Ile Ala Trp Ile Tyr Ser Glu Phe Leu Glu
                20                  25                  30
Tyr Lys Arg Ser Ser Leu His Ser Lys Val His Ser Asp Asn Asn Leu
            35                  40                  45
Val Glu Leu Gly Glu Val Lys Asn Lys Glu Asp Glu Gly Val Val Leu
        50                  55                  60
Leu Glu Gly Gly Leu Pro Arg Ser Val Ser Thr Lys Phe Tyr Asn Ser
65                  70                  75                  80
Pro Ile Lys Thr Asn Leu Ile Arg Phe Leu Thr Leu Glu Asp Ser Phe
```

```
            85                  90                  95
Leu Ile Glu Asn Arg Ala Thr Leu Arg Ala Met Ala Glu Phe Gly Ala
            100                 105                 110

Ile Leu Phe Tyr Phe Tyr Ile Ser Asp Arg Thr Ser Leu Leu Gly Glu
            115                 120                 125

Ser Lys Lys Asn Tyr Asn Arg Asp Leu Phe Leu Phe Leu Tyr Cys Leu
            130                 135                 140

Leu Ile Ile Val Ser Ala Met Thr Ser Leu Lys Lys His Asn Asp Lys
145                 150                 155                 160

Ser Pro Ile Thr Gly Lys Ser Ile Leu Tyr Leu Asn Arg His Gln Thr
                    165                 170                 175

Glu Glu Trp Lys Gly Trp Met Gln Val Leu Phe Leu Met Tyr His Tyr
                    180                 185                 190

Phe Ala Ala Ala Glu Ile Tyr Asn Ala Ile Arg Val Phe Ile Ala Ala
                    195                 200                 205

Tyr Val Trp Met Thr Gly Phe Gly Asn Phe Ser Tyr Tyr Tyr Ile Arg
            210                 215                 220

Lys Asp Phe Ser Leu Ala Arg Phe Thr Gln Met Met Trp Arg Leu Asn
225                 230                 235                 240

Leu Phe Val Ala Phe Ser Cys Ile Ile Leu Asn Asn Asp Tyr Met Leu
                    245                 250                 255

Tyr Tyr Ile Cys Pro Met His Thr Leu Phe Thr Leu Met Val Tyr Gly
                    260                 265                 270

Ala Leu Gly Ile Phe Ser Arg Tyr Asn Glu Ile Pro Ser Val Met Ala
                    275                 280                 285

Leu Lys Ile Ala Ser Cys Phe Leu Val Val Ile Val Met Trp Glu Ile
            290                 295                 300

Pro Gly Val Phe Glu Ile Phe Trp Ser Pro Leu Thr Phe Leu Leu Gly
305                 310                 315                 320

Tyr Thr Asp Pro Ala Lys Pro Glu Leu Pro Leu Leu His Glu Trp His
                    325                 330                 335

Phe Arg Ser Gly Leu Asp Arg Tyr Ile Trp Ile Ile Gly Met Ile Tyr
                    340                 345                 350

Ala Tyr Phe His Pro Thr Val Glu Arg Trp Met Glu Lys Leu Glu Glu
                    355                 360                 365

Cys Asp Ala Lys Arg Lys Met Ser Ile Lys Thr Ser Ile Ile Ala Ile
370                 375                 380

Ser Ser Phe Val Gly Tyr Leu Trp Tyr Glu Tyr Ile Tyr Lys Leu Asp
385                 390                 395                 400

Lys Val Thr Tyr Asn Lys Tyr His Pro Tyr Thr Ser Trp Ile Pro Ile
                    405                 410                 415

Thr Val Tyr Ile Cys Leu Arg Asn Ser Thr Gln Gln Leu Arg Asn Phe
                    420                 425                 430

Ser Met Thr Leu Phe Ala Trp Leu Gly Lys Ile Thr Leu Glu Thr Tyr
            435                 440                 445

Ile Ser Gln Phe His Ile Trp Leu Arg Ser Asn Val Pro Asn Gly Gln
            450                 455                 460

Pro Lys Trp Leu Leu Cys Ile Ile Pro Glu Tyr Pro Met Leu Asn Phe
465                 470                 475                 480

Met Leu Val Thr Ala Ile Tyr Val Leu Val Ser His Arg Leu Phe Glu
                    485                 490                 495

Leu Thr Asn Thr Leu Lys Ser Val Phe Ile Pro Thr Lys Asp Asp Lys
                    500                 505                 510
```

-continued

Arg Leu Leu His Asn Val Leu Ala Gly Ala Ala Ile Ser Phe Cys Leu
515                 520                 525

Tyr Leu Thr Ser Leu Ile Leu Leu Gln Ile Pro His
530                 535                 540

<210> SEQ ID NO 4
<211> LENGTH: 584
<212> TYPE: PRT
<213> ORGANISM: Arabidopsis thaliana

<400> SEQUENCE: 4

Met Asp Pro Val Asp Met Val Val Ser Gln Pro Ile Thr Pro Gly Gln
1               5                   10                  15

Val Ser Phe Leu Leu Gly Val Ile Pro Leu Met Ile Ala Trp Leu Tyr
                20                  25                  30

Ser Glu Phe Leu Glu Tyr Arg Arg Ser Phe His Ala Lys Val His
            35                  40                  45

Ser Asp Lys Asn Leu Val Glu Leu Glu Met Val Thr Asn Lys Glu Asp
        50                  55                  60

Glu Gly Thr Val Leu Met Glu Gly Gly Leu Pro Arg Ser Ala Ser Ser
65                  70                  75                  80

Lys Phe Tyr Ser Ser Pro Ile Lys Thr Asn Leu Ile Arg Phe Leu Thr
                85                  90                  95

Leu Glu Asp Ser Phe Leu Leu Glu Asn Arg Ala Thr Leu Arg Ala Met
            100                 105                 110

Ala Glu Phe Gly Ala Ile Leu Leu Tyr Phe Tyr Ile Cys Asp Arg Thr
        115                 120                 125

Ser Leu Ile Gly Gln Ser Gln Lys Asn Tyr Ser Arg Asp Leu Phe Leu
    130                 135                 140

Phe Leu Phe Cys Leu Leu Ile Ile Val Ser Ala Met Thr Ser Leu Lys
145                 150                 155                 160

Lys His Thr Asp Lys Ser Pro Ile Thr Gly Lys Ser Ile Leu Tyr Leu
                165                 170                 175

Asn Arg His Gln Thr Glu Glu Trp Lys Gly Trp Met Gln Val Leu Phe
            180                 185                 190

Leu Met Tyr His Tyr Phe Ala Ala Val Glu Phe Tyr Asn Ala Ile Arg
        195                 200                 205

Val Phe Ile Ala Gly Tyr Val Trp Met Thr Gly Phe Gly Asn Phe Ser
    210                 215                 220

Tyr Tyr Tyr Ile Arg Lys Asp Phe Ser Leu Ala Arg Phe Thr Gln Val
225                 230                 235                 240

Arg Ser Thr Ile Phe Asp His His Ser Leu Phe Ser Leu Pro Cys Asp
                245                 250                 255

Val Leu Leu Glu Ser Thr Met Ser Phe Lys Ala Gln Asp Phe Tyr Glu
            260                 265                 270

Ser Phe Tyr Leu Ile Gln Met Met Trp Arg Leu Asn Phe Phe Val Ala
        275                 280                 285

Phe Cys Cys Ile Ile Leu Asn Asn Asp Tyr Met Leu Tyr Tyr Ile Cys
    290                 295                 300

Pro Met His Thr Leu Phe Thr Leu Met Val Tyr Gly Ala Leu Gly Ile
305                 310                 315                 320

Tyr Ser Gln Tyr Asn Glu Ile Ala Ser Val Met Ala Leu Lys Ile Ala
                325                 330                 335

Ser Cys Phe Leu Val Val Ile Leu Met Trp Glu Ile Pro Gly Val Phe

```
                340                 345                 350
Glu Ile Phe Trp Ser Pro Leu Ala Phe Leu Leu Gly Tyr Thr Asp Pro
            355                 360                 365

Ala Lys Pro Asp Leu Pro Arg Leu His Glu Trp His Phe Arg Ser Gly
370                 375                 380

Leu Asp Arg Tyr Ile Trp Ile Ile Gly Met Ile Tyr Ala Tyr Phe His
385                 390                 395                 400

Pro Thr Val Glu Arg Trp Met Glu Lys Leu Glu Glu Cys Asp Ala Lys
            405                 410                 415

Arg Arg Met Ser Ile Lys Thr Ser Ile Ile Gly Ile Ser Ser Phe Ala
            420                 425                 430

Gly Tyr Leu Trp Tyr Glu Tyr Ile Tyr Lys Leu Asp Lys Val Thr Tyr
            435                 440                 445

Asn Lys Tyr His Pro Tyr Thr Ser Trp Ile Pro Ile Thr Val Tyr Ile
            450                 455                 460

Cys Leu Arg Asn Cys Thr Gln Gln Leu Arg Arg Phe Ser Leu Thr Leu
465                 470                 475                 480

Phe Ala Trp Leu Gly Lys Ile Thr Leu Glu Thr Tyr Ile Ser Gln Phe
            485                 490                 495

His Ile Trp Leu Arg Ser Ser Val Pro Asn Gly Gln Pro Lys Leu Leu
            500                 505                 510

Leu Ser Ile Ile Pro Glu Tyr Pro Met Leu Asn Phe Met Leu Thr Thr
            515                 520                 525

Ala Ile Tyr Val Leu Val Ser Val Arg Leu Phe Glu Leu Thr Asn Thr
            530                 535                 540

Leu Lys Ser Val Phe Ile Pro Thr Lys Asp Asp Lys Arg Leu Leu His
545                 550                 555                 560

Asn Val Ile Ala Met Ala Ala Ile Ser Phe Cys Leu Tyr Ile Ile Gly
            565                 570                 575

Leu Ile Leu Leu Leu Ile Pro His
            580

<210> SEQ ID NO 5
<211> LENGTH: 960
<212> TYPE: PRT
<213> ORGANISM: Cryptococcus neoformans

<400> SEQUENCE: 5

Met Pro Asn Ser Ser Lys Pro Arg Ser Gln Ala Ser Ala Ala Lys Leu
1               5                   10                  15

Asn Pro Leu Trp Tyr Thr Tyr Ala Cys Ala Thr Leu Val Ala Ala Val
            20                  25                  30

Val Leu Gly Asn Ile Leu Arg Trp Ala Phe Leu Glu Leu Pro Asp Ser
        35                  40                  45

Tyr His Cys Ser Ala Leu Leu Asn Thr Gly Lys Trp Leu Asp Pro Gly
    50                  55                  60

Thr Trp Thr Asn Trp Gln Pro Glu Gly Cys Phe Gln Leu Pro Leu Ser
65                  70                  75                  80

Ala Gln Ser Trp Gln Lys Cys Leu Ala Ser Pro Thr Val Asn Thr His
            85                  90                  95

Gln Ala Leu His Ser Ser Tyr Tyr Asp Lys Arg Thr Ala Leu Phe Val
            100                 105                 110

Gly Asp Ser Thr Val Arg Gln Leu Tyr Phe Ala Ala Ala Arg Lys Val
        115                 120                 125
```

```
Gly Lys Thr Ser Lys Ala Trp Glu Leu Glu Gly Glu Lys His Thr Asp
        130                 135                 140
Arg Ser Leu Leu Val Ser Asp Pro Leu Gly Pro Ser Leu Glu Leu
145                 150                 155                 160
Glu Phe Trp Trp Asp Pro Tyr Leu Asn Ser Ser Lys Thr Ile Gly Leu
                    165                 170                 175
Leu Ser Gly Gln Ser Ser Val Pro Ser Ser Leu Leu Val Met Gly Ser
                180                 185                 190
Gly Leu Trp Tyr Leu Arg Asn Pro Ser Ser Gly Gly Leu Ala Ser Trp
            195                 200                 205
Gly Ala Met Ile Tyr Asp Thr Phe Glu Leu Val Lys Lys Asn Gln Gly
        210                 215                 220
Ser Pro Gln Thr Ala Leu Ile Asn Pro Trp Asp Asn Met Leu Leu Gly
225                 230                 235                 240
Pro Gly Ile Thr Leu Pro Gly Leu Leu Pro Asn Gln Pro Pro Lys Phe
                    245                 250                 255
Val Asp His Ser Arg Glu Val Glu Ala Arg Ser Leu Phe Ser Arg Ala
                260                 265                 270
Ser Ser Ile Ser His Arg Pro Thr Asp Phe Ser Ile Ser Asp Ala Ile
            275                 280                 285
Val Phe Leu Pro Ile Ser Thr Pro Val Arg Glu Lys Leu Ser Pro Ser
        290                 295                 300
Arg Ala Glu Thr Ile Phe His Thr Asp Val Glu Ala Met Asn Ala Asp
305                 310                 315                 320
Leu Tyr Ala Arg Leu Thr His Pro Asp Pro Pro Val Val Ile Pro
                    325                 330                 335
Ser Val Leu Asn Gln Leu Leu Val Asp Asp Glu Thr Glu Asp Gly Leu
                340                 345                 350
His Phe Ser Asp Lys Ile Met Asn Lys Gln Ala Glu Leu Leu Leu Ser
            355                 360                 365
Trp Arg Cys Asn Asp Val Met Arg His Glu Gly Ala Thr Gly Thr Cys
        370                 375                 380
Cys Lys Arg Tyr Asp Trp Val Thr Pro Ile Gln Gly Leu Ile Leu Ala
385                 390                 395                 400
Val Leu Ile Leu Trp Ala Pro Leu Gly Thr Phe Ile Thr Pro Arg Leu
                    405                 410                 415
Pro Pro Asn Ser Pro Ile Leu Asp Tyr Leu Pro Ala Thr Ser Ile Ala
                420                 425                 430
Pro Ala Leu Ser Thr Phe Gly Leu Ala Met Gly Tyr Leu Phe Leu Ala
            435                 440                 445
Asp Arg Thr His Val Phe Gln Lys Glu Gln Lys Asp Tyr Asp Ala Val
        450                 455                 460
Ile Phe Gly Met Ile Thr Leu Ala Ala Phe Val Ala Gly Leu Leu Thr
465                 470                 475                 480
Ile Lys Asn Ser Gly Lys Asp Leu Gly Phe Leu Asn Arg Asp Ile Thr
                    485                 490                 495
Asp Glu Trp Lys Gly Trp Met Gln Ile Ala Ile Leu Ile Tyr His Phe
                500                 505                 510
Phe Gly Ala Ser Lys Ile Ser Gly Ile Tyr Asn Pro Ile Arg Val Leu
            515                 520                 525
Val Ala Ser Tyr Leu Phe Met Thr Gly Tyr Gly His Phe Phe Phe Tyr
        530                 535                 540
Tyr Lys Lys Ala Asp Phe Gly Phe Gln Arg Val Val Met Val Leu Val
```

-continued

```
            545                 550                 555                 560
Arg Leu Asn Leu Leu Ser Val Leu Pro Tyr Thr Met Asn Thr Asp
                565                 570                 575
Tyr Ala Phe Tyr Tyr Phe Ala Pro Leu Val Ser Trp Trp Tyr Leu Ile
                    580                 585                 590
Ile Tyr Ala Thr Met Ala Ile Gly Ser Lys Tyr Asn Asp Arg Pro Ala
                595                 600                 605
Phe Leu Leu Thr Lys Leu Phe Thr Cys Ala Gly Leu Val Thr Leu Phe
    610                 615                 620
Met His Phe Pro Trp Leu Met Glu Asp Val Phe Lys Val Leu Asn Thr
625                 630                 635                 640
Val Phe Asn Ile Gln Trp Ser Ala Lys Glu Trp Ser Phe Arg Val Thr
                645                 650                 655
Leu Asp Leu Phe Ile Val Trp Val Gly Met Leu Cys Ala Tyr Gly Phe
                660                 665                 670
Val Lys Phe Asn Glu His Gln Ile Ser Asp Arg Pro Trp Phe Pro Val
                675                 680                 685
Met Arg Thr Ala Thr Leu Val Gly Ser Val Leu Gly Met Ile Trp Tyr
    690                 695                 700
Phe Trp Phe Glu Leu His Leu Ala Ser Lys Phe Val Tyr Asn Glu Tyr
705                 710                 715                 720
His Ala Val Val Cys Ile Val Pro Ile Met Ser Phe Val Phe Leu Arg
                725                 730                 735
Asn Ala Ser Pro Val Leu Arg Ser Ser Thr Ser Lys Ile Phe Cys Phe
                740                 745                 750
Ile Gly Gln Cys Ser Leu Glu Thr Phe Ile Leu Gln Phe His Gly Trp
                755                 760                 765
Leu Ala Ser Asp Thr Lys Ala Ile Leu Ala Val Pro Ser Thr Gln
    770                 775                 780
Trp Arg Pro Val Asn Leu Val Ile Ser Thr Ile Cys Phe Ile Trp Leu
785                 790                 795                 800
Ser Tyr Arg Val Ser Gly Ala Thr Gly Glu Ile Thr Glu Trp Leu Val
                805                 810                 815
Gly Lys Lys Lys Ala Leu Pro Leu Pro Ala Thr Ser Ala Asn Ser Ser
                820                 825                 830
Thr Ser Pro Gly Arg Gln Ala Thr Ser Pro Thr Leu Thr Ser Ala Ser
    835                 840                 845
Ala Met Gln Ala Val Val Gly Pro Gln Asp Gly Ala Lys Gly Gly
    850                 855                 860
Ile Pro Glu Ser Ile Pro Met Met Asn Gln Ala Asp Lys Asp Ile Gly
865                 870                 875                 880
Gly Leu Thr Pro Met Glu Asp Glu Thr Leu Glu Arg Arg Asp Ser Trp
                885                 890                 895
Pro Thr Trp Met Ala Ser Thr Ala Ala Ser Leu Thr Gly Arg Thr Val
                900                 905                 910
Glu Gly Tyr Ala Pro Leu Thr Arg Arg Trp Lys Asp Gln Thr Val Leu
                915                 920                 925
Ser Val Ile Gln Asn Leu Gly Asp Leu Met Lys Lys His Asn Ser Val
                930                 935                 940
Lys Ile Ala Val Ile Leu Leu Gly Leu Trp Ala Leu Asn Trp Ile Tyr
945                 950                 955                 960
```